US006536433B1

(12) United States Patent
Cewers

(10) Patent No.: US 6,536,433 B1
(45) Date of Patent: Mar. 25, 2003

(54) DIRECTIONAL VALVE

(75) Inventor: Göran Cewers, Lund (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/550,114

(22) Filed: Apr. 14, 2000

(30) Foreign Application Priority Data

Apr. 27, 1999 (SE) .............................................. 9901511

(51) Int. Cl.$^7$ .......................... A61M 16/00; F16K 31/02
(52) U.S. Cl. ............................ 128/205.24; 128/204.18; 128/204.21; 128/204.23; 251/129.1
(58) Field of Search ................... 128/205.24, 204.18, 128/204.21, 204.23; 251/129.1

(56) References Cited

U.S. PATENT DOCUMENTS

| 4,506,861 A | | 3/1985 | Showalter |
| 4,511,118 A | | 4/1985 | Kühl et al. |
| 4,595,170 A | * | 6/1986 | Livet ..................... 251/129.01 |
| 4,612,845 A | * | 9/1986 | Burkel et al. ................. 91/448 |
| 4,715,264 A | * | 12/1987 | Stoll ..................... 251/129.02 |
| 5,628,296 A | * | 5/1997 | Herrington et al. .... 123/568.21 |
| 5,678,521 A | * | 10/1997 | Thompson et al. .......... 123/446 |
| 5,704,586 A | * | 1/1998 | Nielsen ....................... 137/554 |
| 5,722,632 A | * | 3/1998 | Rader et al. ............ 123/568.27 |
| 6,092,782 A | * | 7/2000 | Yamada et al. .............. 222/571 |
| 6,095,490 A | * | 8/2000 | Nakano et al. ......... 251/129.17 |
| 6,220,242 B1 | * | 4/2001 | Wallin .................... 128/203.12 |
| 6,289,922 B1 | * | 9/2001 | Nakano et al. .......... 137/454.6 |

FOREIGN PATENT DOCUMENTS

| FR | 2185176 | 12/1973 |
| GB | 968017 | 8/1964 |

* cited by examiner

Primary Examiner—Aaron J. Lewis
Assistant Examiner—Mital Patel
(74) Attorney, Agent, or Firm—Schiff Hardin & Waite

(57) ABSTRACT

A directional valve for respiratory devices has a valve body and a valve seat whose contact surface with the valve body is primarily horizontal. In order to enhance and reinforce the directional valve's operation, the valve body contains a ferromagnetic material, preferably permanently magnetized, a coil is magnetically couplable to the valve body, a source of current is connected to the coil, and a control unit controls the source of current in order to regulate current through the coil to magnetically couple the coil to the valve body, in one or both of the closing and opening directions.

10 Claims, 2 Drawing Sheets

DIRECTIONAL VALVE

BACKGROUND OF THE INVENTION

1. Field of the Invention

The present invention relates to a directional valve suitable for use in respiratory devices, the directional valve being of the type having a valve body and a valve seat with the contact surface with the valve body being substantially horizontal.

2. Description of the Prior Art

Directional valves are used in respiratory devices, anaesthetic machines in particular, to channel the direction of gas flow. One directional valve is generally installed in the anaesthetic machine's inspiratory line and one directional valve in its expiratory line. Ideally, the directional valves should not affect expiratory resistance and inspiratory resistance for the patient nor interfere with measurements of flow in the anaesthetic machine. A conventional way to meet these conditions has been to devise directional valves with the lowest possible opening pressure. Such valves therefore generally are devised as disk valves, i.e. the directional valve has a disk-shaped valve body that rests loosely on a valve seat.

This type of directional valve has disadvantages. One disadvantage arises because moist gas is present in the anaesthetic machine. The valve body sometimes becomes wet, leading to surface tension that increases the opening pressure.

Other disadvantages are due to the shape of the valve body. If it is devised as a soft, lightweight disk, retrograde leakage could occur. Moreover, the valve body could be deformed enough by high back pressures to be pushed down into the valve opening. This would naturally be a serious problem, since the directional valve would then stop working. Retrograde leakage can be reduced by the use of a heavier directional valve, but this would naturally increase the valve's opening pressure, and the valve body might then start wobbling. Stiff valve bodies (usually ceramic disks) could start to leak because of the deposition of calcium particles etc. on the valve seat.

SUMMARY OF THE INVENTION

An object of the present invention is to provide a directional valve that solves the aforementioned problems.

The above object is achieved in accordance with the principles of the present invention in a directional valve for a respiratory device, having a valve body and a valve seat, the contact surface of the valve seat with the valve body being substantially horizontal and the valve body containing ferromagnetic material, and the directional valve further having at least one coil which is magnetically couplable to the valve body, a source of current connected to the coil, and a control unit which regulates the current source to control the current through the coil so that the coil is magnetically coupled to the valve body in one or both of a closing direction and an opening direction.

When the valve body contains a ferromagnetic material and two coils are arranged with one coil on top of the valve body and one coil underneath the valve body, the valve body can be made to press against the valve seat or alternately lift off the valve seat by regulating the current flowing through the respective coils.

The directional valve can be operated as a servo system in an embodiment wherein the valve body contains a permanently magnetized material and a coil encircles the valve body and valve opening (to achieve the strongest possible magnetic coupling between the coil and the valve body). When the directional valve is to be in the closed position, a current is applied across the coil, generating a magnetic field that presses the valve body harder against the valve seat. This would accordingly reduce the risk of leakage.

When the directional valve is to be in the open position, the current is reversed, causing the electromagnetic field to lift the valve body. A minimal opening pressure is then achieved.

In the event of any loss of current, the directional valve would operate in the same way as a conventional directional valve. Directional valve operation is not interrupted. This is an important safety feature when the valve is used in anaesthetic machines and other respiratory devices.

Current through the coil is regulated from a source of current that is regulated, in turn, by a control unit. In principle, the control unit could regulate the source of current in such a way that directional valve operation parallels the respiratory device's inspiratory and expiratory phases. The directional valve in the inspiratory line would then be open during inspiration and closed during expiration (and the reverse for the directional valve in the expiratory line). This kind of simplified regulation is only possible in certain limited conditions, e.g. no bias flow is used and the patient is not breathing spontaneously.

More refined regulation, tailored to different phases of respiration, e.g. during anaesthesia, is possible. The control unit therefore can control the source of current by sensing the valve body's position. This can be achieved by inductive sensing of the coil. Alternatively, the EMF generated by the valve body's movements can be sensed and employed for controlling the source of current. Any deformation of the valve body can even be sensed from changes in inductance.

Other parameters can also be used for regulation, for example, the pressure gradient between the inlet and outlet sides of the directional valve and flow through the directional valve. These parameters can be obtained either by providing the directional valve with a pressure gauge or a flow meter or by utilizing measurement signals from existing pressure gauges or flow meters in the respiratory device.

DESCRIPTION OF THE PREFERRED EMBODIMENTS

Figure 1:
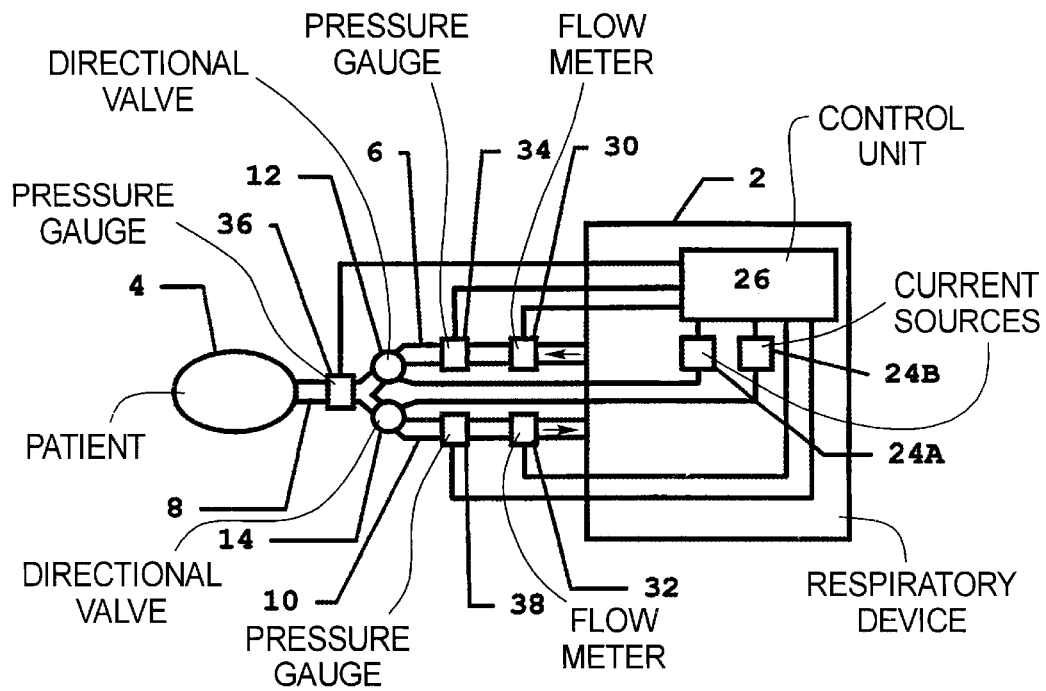
FIG. 1 shows a respiratory device incorporating directional valves according to the invention.

FIG. 1 shows a respiratory device 2 connected to a patient 4, in the conventional, known fashion, by an inspiratory line 6, a patient line 8 and an expiratory line 10. The respiratory device 2 can e.g. be an anaesthetic machine, and the patient line 8 can be a tracheal tube and Y-piece.

A first directional valve 12 is arranged in the inspiratory line 6 (or between the inspiratory line 12 and the patient line 8), and a second directional valve 14 is arranged in the expiratory line 10 (or between the expiratory line 10 and the patient line 8).

The function of the directional valves 12, 14 is mainly to achieve one-way passage of gas through the lines 6, 8, 10;

therefore they must not allow any retrograde leakage. At the same time, it is undesirable for the directional valves 12, 14 to create any additional respiratory resistance for the patient 4 during inspiration and expiration. They must therefore open easily in the forward direction.

Figure 2:
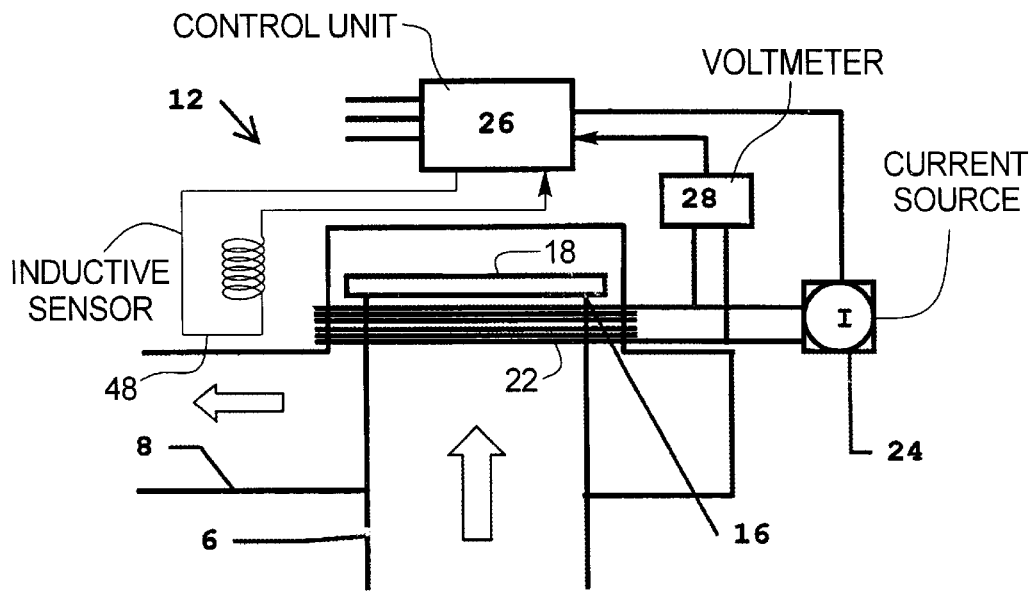
FIG. 2 shows a first embodiment of the inventive directional valve.

FIG. 2 shows a first embodiment of the first directional valve 12 (the second has an identical construction). In this instance, the inspiratory line 6 is connected to the inlet side of the first directional valve 12, and the patient line 8 is connected to the outlet side of the first directional valve 12. The first directional valve 12 has an essentially, horizontal valve seat 16. A valve body 18 rests on the valve seat 16. In this embodiment, the valve body 18 is disk-shaped, but other designs are possible. The surface of the valve body 18 in contact with the valve seat 16 is preferably made of a soft material. A hood 20 encircles the valve seat 16 and the valve body 18. The hood 20 is preferably transparent to permit visual inspection by the operator.

A coil 22 surrounds part of the first directional valve 12 for magnetic coupling to the valve body 18 that contains, or consists of, a permanently magnetized ferromagnetic material. When a current is applied to the coil 22 from a source of current 24, the valve body 18 is either pressed against the valve seat 16 or lifted off the valve seat 16, depending on the direction of current in the coil. The basic functions of the directional valve 12 accordingly can be maintained without loss in the event of a power failure. This is extremely important to patient safety.

The source of current 24 is regulated by a control unit 26 on the basis of suitable control parameters. Some of these control parameters can be obtained from changes in EMF, induction etc. in the coil 22 occurring when the valve body 18 is affected by gases in the lines 6, 8. Determination of these parameters can be performed by e.g. measuring voltage across the coil 22 with a voltmeter 28 and sending the measured value to the control unit 26. (Alternatively or as a complement, current in the coil 22 can be measured inductively by sensor 48 and the measured value sent to the control unit 26.)

Referring again to FIG. 1. The control unit 26 in the depicted embodiment is integrated into the respiratory device 2 and controls a first source of current 24A for regulating the first directional valve 12 and a second source of current 24B for regulating the second directional valve 14. Alternatively, a separate control unit (in the form of a microchip or the equivalent) can be integrated into the respective directional valves 12, 14.

Additional opportunities for obtaining control parameters are provided with a first flow meter 30 in the inspiratory line 6, a second flow meter 32 in the expiratory line 10, a first pressure gauge 34 in the inspiratory line 6, a second pressure gauge 36 in the patient line 8 and a third pressure gauge 38 in the expiratory line 10. Flow through the respective directional valves 12, 14 or the pressure gradient between the inlet and outlet sides of the respective directional valves 12, 14 can be determined and used by the control unit 26 for regulating the directional valves 12, 14.

The flow meters and pressure gauges 30, 32, 34, 36, 38 can be formed by components integrated into the directional valves 12, 14 or of components in the respiratory device 2 (or any combination thereof).

Regulation is suitably performed in such a way that the control unit 26, via the sources of current 24A, 24B and with the aid of the parameters, regulates the directional valves 12, 14 by reinforcing their natural positions (open-closed) in every phase of the respiratory cycle. For many applications, the control unit 26 can suitably be supplied even with information from the respiratory device's control system on the respiratory cycles etc. Alternatively, the control unit 26 can even be an integral part of the control and regulatory system of the respiratory device 2.

Figure 3:
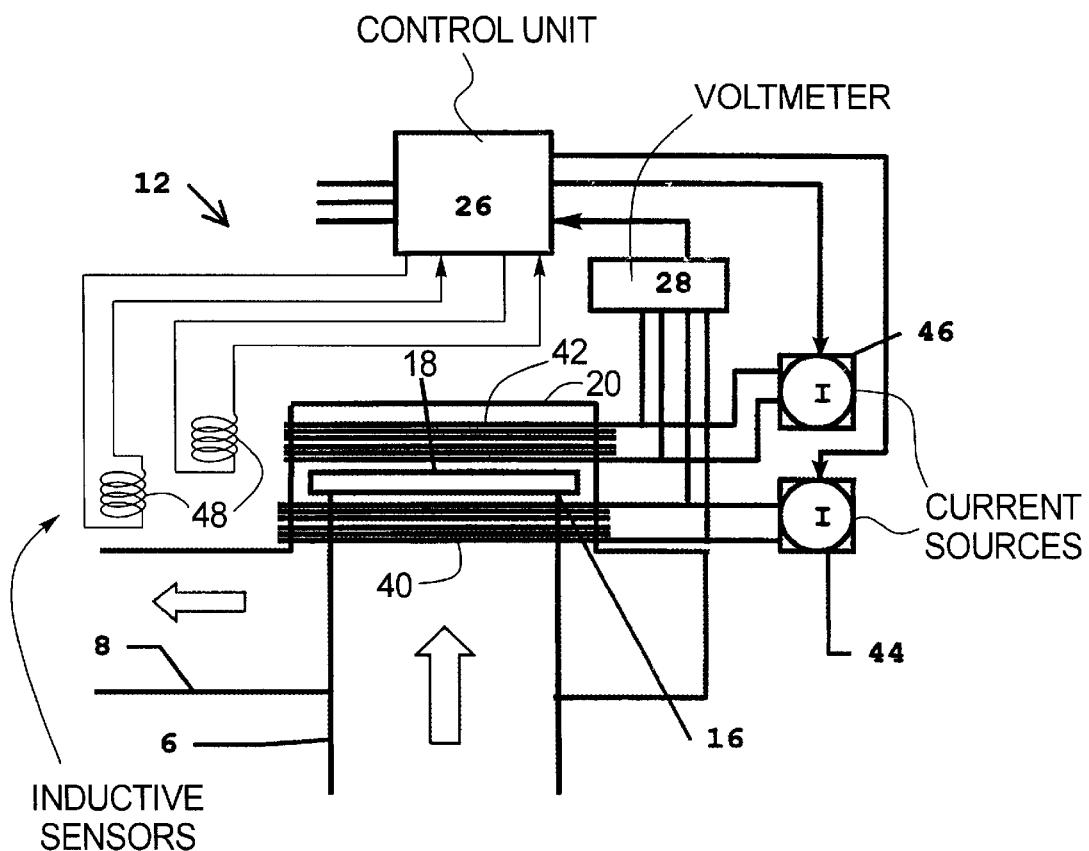
FIG. 3 shows a second embodiment of the inventive directional valve.

FIG. 3 shows a second embodiment of the directional valve 12. As in the first embodiment, the inspiratory line 6 is connected to the inlet side of the directional valve 12, and the patient line 8 is connected to the outlet side of the first directional valve 12. The first directional valve 12 has a mainly horizontal valve seat 16. A disk-shaped valve body 18 rests on the valve seat 16. The valve body 18 preferably is made of a soft material at points at which it is in contact with the valve seat 16. A hood 20 encircles the valve seat 16 and valve body 18. The hood 20 is preferably transparent to permit visual inspection by the operator.

In this second embodiment, the direction valve 12 contains a first coil 40, arranged below the valve body 18, and a second coil 42, arranged above the valve body 18. The valve body contains, or consists of, a ferromagnetic material.

A current can be applied to the first coil 40 from a first source of current 44, and a current can be applied to the second coil 42 from a second source of current 46. The sources of current 44, 46 are regulated by a control unit 26 on the basis of suitable control parameters in the same way as in the first embodiment. These parameters can be obtained from a voltmeter 28, straight from the sources of current 44, 46 or in some other way described above, such as with inductive sensors 48. The sources of current 41, 46 in this embodiment are regulated differently, since current is alternately applied to the first coil 40 and the second coil 42 respectively.

Other embodiments of the directional valves are possible. For example, the coil(s) can be located in other ways with retention of the same functions.

Although modifications and changes may be suggested by those skilled in the art, it is the intention of the inventor to embody within the patent warranted hereon all changes and modifications as reasonably and properly come within the scope of his contribution to the art.

I claim as my invention:

1. A directional valve for a respiratory device, said directional valve comprising:

a valve body containing ferromagnetic material;

a valve seat having a valve opening surrounded by a substantially horizontal contact surface on which said valve body loosely rests, said valve body being forced to move in an opening direction to open said valve opening exclusively by a fluid flow in one direction through said valve opening, and to move in a closing direction to close said valve opening exclusively due to said fluid flow ceasing or changing to a direction opposite said one direction;

at least one coil which is magnetically couplable to said valve body;

a current source connected to said coil; and a control unit which regulates said current source to control a current through said coil to magnetically couple said coil to said valve body in at least one of said closing direction, to tightly close said valve opening, and said opening direction, to promote opening of said valve opening.

2. A directional valve as claimed in claim 1 wherein said control unit regulates said current through said coil to magnetically couple said coil to said valve body in each of said closing direction and said opening direction.

3. A directional valve as claimed in claim 1 wherein said ferromagnetic material is permanently magnetized.

4. A directional valve as claimed in claim 1 further comprising an inductive sensor which senses a position of said valve body, and wherein said control unit is connected to said inductive sensor and regulates said current source dependent on said position of said valve body.

5. A directional valve as claimed in claim 1 wherein movement of said valve body generates a voltage across said coil, and further comprising a sensor which senses said voltage due to said movement of said valve body, said control unit being connected to said sensor and regulating said current source dependent on said movement of said valve body.

6. A directional valve as claimed in claim 1 wherein deformation of said valve body generates a voltage across said coil, and further comprising a sensor which senses said voltage due to said deformation of said valve body, said control unit being connected to said sensor and regulating said current source dependent on said deformation of said valve body.

7. A directional valve as claimed in claim 1 further comprising an inductive sensor which measures a change in inductance in said coil caused by deformation of said valve body, and wherein said control unit is connected to said inductive sensor and regulates said current source dependent on said deformation of said valve body.

8. A directional valve as claimed in claim 1 wherein said valve seat has an inlet side and an outlet side, and further comprising a first pressure gauge which measures an inlet pressure at said inlet side and a second pressure gauge which measures an outlet pressure at said outlet side, and wherein said control unit is connected to said first pressure gauge and to said second pressure gauge and determines a pressure gradient between said inlet pressure and said outlet pressure, and wherein said control unit regulates said current source dependent on said pressure gradient.

9. A directional valve as claimed in claim 1 further comprising a flow meter which measures a flow through said valve opening, and wherein said control unit is connected to said flow meter and regulates said current source dependent on said flow.

10. A directional valve for a respiratory device, said directional valve comprising:

a valve body containing ferromagnetic material;

a valve seat having a valve opening surrounded by a substantially horizontal contact surface for said valve body, said valve body being disposed to move in a closing direction to close said valve opening and in an opening direction to open said valve opening;

a first coil which is magnetically couplable to said valve body, said first coil being disposed at a first side of said valve body and said valve opening;

a first current source connected to said first coil for producing a first current in said first coil;

a second coil which is magnetically couplable to said valve body, said second coil being disposed at a second side of said valve body and said opening opposite to said first side;

a second current source connected to said second coil for producing a second current in said second coil; and a control unit connected to said first current source and to said second current source for regulating said first current and said second current to magnetically couple at least one of said first and second magnetic coils to said valve body in said opening direction and to magnetically couple at least one of said first and second coils to said valve body in said closing direction.

* * * * *